(12) United States Patent
Walsh (10) Patent No.: US 9,795,492 B1
(45) Date of Patent: Oct. 24, 2017

(54) MAGNETICALLY CONNECTABLE INTERBODY SPINAL IMPLANT DEVICES

(71) Applicant: NuVasive, Inc., San Diego, CA (US)

(72) Inventor: Christopher Walsh, Jupiter, FL (US)

(73) Assignee: NuVasive, Inc., San Diego, CA (US)

( * ) Notice: Subject to any disclaimer, the term of this patent is extended or adjusted under 35 U.S.C. 154(b) by 203 days.

(21) Appl. No.: 14/216,509

(22) Filed: Mar. 17, 2014

Related U.S. Application Data (63) Continuation-in-part of application No. 13/874,274, filed on Apr. 30, 2013.

(60) Provisional application No. 61/640,378, filed on Apr. 30, 2012, provisional application No. 61/788,147, filed on Mar. 15, 2013.

(51) Int. Cl.
*A61F 2/44* (2006.01)

(52) U.S. Cl.
CPC ........ *A61F 2/447* (2013.01); *A61F 2002/448* (2013.01)

(58) Field of Classification Search
CPC .......... A61F 2/44; A61F 2/4455; A61F 2/446; A61F 2/4465; A61F 2/447; A61F 2002/4475; A61F 2002/448; A61F 2002/4485
USPC ........................................... 623/17.11–17.16
See application file for complete search history.

(56) References Cited

U.S. PATENT DOCUMENTS

| 4,349,921 | A | * | 9/1982 | Kuntz | A61F 2/4425 623/17.16 |
|---|---|---|---|---|---|
| 5,192,327 | A | * | 3/1993 | Brantigan | A61F 2/44 606/247 |
| 5,522,899 | A | * | 6/1996 | Michelson | A61F 2/30744 606/279 |
| 5,861,041 | A | * | 1/1999 | Tienboon | A61F 2/4455 606/247 |
| 6,110,210 | A | * | 8/2000 | Norton | A61F 2/441 623/17.11 |
| 6,350,283 | B1 | * | 2/2002 | Michelson | A61F 2/4455 623/17.11 |
| 7,591,853 | B2 | * | 9/2009 | Felt | A61F 2/4611 606/249 |
| 8,137,403 | B2 | * | 3/2012 | Michelson | A61F 2/28 623/17.11 |
| 2002/0183761 | A1 | * | 12/2002 | Johnson | A61B 17/025 606/90 |
| 2004/0093085 | A1 | * | 5/2004 | Michelson | A61F 2/4455 623/17.11 |
| 2006/0015184 | A1 | * | 1/2006 | Winterbottom | A61F 2/44 623/18.11 |
| 2006/0189999 | A1 | * | 8/2006 | Zwirkoski | A61F 2/442 606/90 |

(Continued)

*Primary Examiner* — Eric S Gibson
(74) *Attorney, Agent, or Firm* — Rory Schermerhorn; Jennifer Russell; NuVasive, Inc.

(57) ABSTRACT

The present invention provides for an improved spinal implant which is useful in bone fixation surgeries. The spinal implant as described herein provides a surgeon with a device that can easily and safely be inserted into the space previously occupied by the spinal disc. The spinal implant contains one or more magnets positioned on or within the device to self-align with one or more additional spinal implants inserted therein for the purpose of preventing misalignment of a plurality of implant devices during surgical procedures and preventing implant expulsion.

8 Claims, 12 Drawing Sheets

(56) References Cited

U.S. PATENT DOCUMENTS

| | | | |
|---|---|---|---|
| 2008/0119853 A1* | 5/2008 | Felt | A61F 2/4611 606/258 |
| 2008/0133017 A1* | 6/2008 | Beyar | A61F 2/4425 623/17.16 |
| 2008/0249622 A1* | 10/2008 | Gray | A61F 2/4455 606/86 A |
| 2008/0312743 A1* | 12/2008 | Vila | A61F 2/442 623/17.16 |
| 2009/0138086 A1* | 5/2009 | Dewey | A61F 2/44 623/17.16 |
| 2011/0257749 A1* | 10/2011 | Fleischmann | A61F 2/38 623/17.16 |
| 2013/0018467 A1* | 1/2013 | Suh | A61F 2/44 623/17.16 |

* cited by examiner

MAGNETICALLY CONNECTABLE INTERBODY SPINAL IMPLANT DEVICES

CROSS-REFERENCE TO RELATED APPLICATIONS

This application is a continuation-in-part of U.S. application Ser. No. 13/874,274 filed Apr. 30, 2013, now pending, which claims the benefit of priority from U.S. Provisional Application 61/460,378 filed Apr. 30, 2012. This application also claims the benefit of priority from U.S. Provisional Application No. 61/788,147 filed on Mar. 15, 2013. The contents of U.S. Application No. 61/788,147, Ser. No. 13/874,274, and 61/460,378 are incorporated by reference as part of this application.

FIELD OF THE INVENTION

The present invention relates to surgical implant devices useful for stabilization of adjacent bony structures of the spine, and more particularly to self aligning interbody spinal implants adapted to aligning with other aligning interbody spinal implant devices during spinal procedures such as bone fusion/fixation procedures.

BACKGROUND OF THE INVENTION

The central nervous system is a vital part of the human physiology that coordinates human activity. It is primarily made up of the brain and the spinal chord. The spinal chord is made up of a bundle of nerve tissue which originates in the brain and branches out to various parts of the body, acting as a conduit to communicate neuronal signals from the brain to the rest of the body, including motor control and sensations. Protecting the spinal chord is the spinal, or vertebral, column. Anatomically, the spinal column is made up of several regions, including the cervical, thoracic, lumbar and sacral regions. The cervical spine is made up of seven vertebrae and functions to support the weight of the head. The thoracic spine is made up of 12 vertebrae and functions to protect the organs located within the chest. Five vertebrae make up the lumbar spine. The lumbar spine contains the largest vertebra and functions as the main weight bearing portion of the spine. Located at the base of the spine is the five fused vertebrae known as the sacrum. The coccyx sits at the base of the spinal column and consists of four fused vertebrae.

Each of the vertebrae associated with the various spinal chord regions are made up of a vertebral body, a posterior arch, and transverse processes. The vertebral body, often described as having a drum-like shape, is designed to bear weight and withstand compression or loading. In between the vertebral bodies is the intervertebral disc. The intervertebral disc is filled with a soft, gelatinous-like substance which helps cushion the spine against various movements and can be the source of various diseases. The posterior arch of the vertebrae is made up of the lamina, pedicles and facet joints. Transverse processes extend outwardly from the vertebrae and provide the means for muscle and ligament attachment, which aid in movement and stabilization of the vertebra.

While most people have fully functional spinal chords, it is not uncommon for individuals to suffer some type of spinal ailment, including spondylolisthesis, scoliosis, or spinal fractures, which are so severe as to require surgical intervention. One of the more common disorders associated with the spinal chord which requires surgical intervention is damage to the spinal discs. Damage to the discs results from physical injury, disease, genetic disposition, or as part of the natural aging process. Disc damage often results in intervertebral spacing not being maintained, causing pinching of exiting nerve roots between the discs, resulting in pain. A disc herniation may compress the spinal cord and/or nerve roots and cause pain, loss of function, and even complete paralysis of the legs with loss of bowel and bladder control.

For most patients, rest and administration of pain and anti-inflammatory medications alleviates the problem. In severe cases, cases which have developed into spinal instability or severe disc degeneration, the damaged disc material between the vertebral bodies is removed and replaced with spinal stabilization implants. Restoration to the normal height allows the pressure on the nerve roots to be relieved. However, removal of the offending discal tissue has proven both difficult and quite dangerous. When the discs of the thoracic spine are approached posteriorly (from behind), the spinal cord is in the way. To approach the same herniation anteriorly (from the front) requires the very formidable procedure of thoracotomy (cutting open the chest) and moving the heart and lungs out of the way.

There are many different approaches taken to alleviate or minimize severe spinal disorders. One surgical procedure commonly used is a spinal fusion technique. Several surgical approaches have been developed over the years, and include the Posterior Lumbar Fusion (PLIF) procedure which utilizes a posterior approach to access the patient's vertebrae or disc space, the Transforaminal Lumbar Fusion (TLIF) procedure which utilizes a posterior and lateral approach to access the patient's vertebrae or disc space, an Anterior Lumbar Fusion (ALIF) which utilizes an anterior approach to access the patient's vertebrae or disc space, or Lateral Interbody Fusion (XLIF) or Direct Lateral Interbody Fusion (DLIF) which utilize a lateral approach to the spine. Using any of these surgical procedures, the patient undergoes spinal fusion surgery in which two or more vertebrae are linked or fused together through the use of a bone spacing device and/or use of bone grafts. The resulting surgery eliminates any movement between the spinal sections which have been fused together.

In addition to the spinal implants or use of bone grafts, spinal fusion surgery often utilizes spinal instrumentation or surgical hardware, such as pedicle screws, plates, or spinal rods. Once the spinal implants and/or bone grafts have been inserted, a surgeon places the pedicle screws into a portion of the spinal vertebrae and attaches either rods or plates to the screws as a means for stabilization while the bones fuse.

While this bone fusion technique often alleviates the pain associated with such disease, implantation of the spinal implant devices can be difficult. Gripping features, as well as various shapes, have been incorporated into the design of implants for ease of insertion and better hold on the vertebral endplates. Implantation is more difficult when the surgeon utilizes multiple implant devices, as proper alignment of the multiple implant devices can be very challenging. Implanting several implant devices can be time consuming, increasing the risk of surgical complications. Once implanted, the implant devices do not always remain at the site of implantation. Implant expulsion results from implants migrating and expelling out of the disc space, usually through the insertion pathway. Implants that migrate to the spinal chord or nerve roots can cause serious complications to the patient. While threaded features or teeth are used to prevent such migration, care must be used when incorporating these features into the design of the implant; as such features can result in localized stress risers in the end plates causing implant subsidence.

There exists, therefore, a need for an improved spinal implant, preferably an interbody spinal implant device, that is easy to insert, is self-aligning when multiple spinal implants are used in a surgical procedure, and reduces the risk of spinal implant expulsion.

SUMMARY OF THE INVENTION

The present invention provides for an improved spinal implant, preferably an interbody spinal implant device, which is useful in surgical procedures that require implants devices, such as bone fusion/fixation surgeries. While the present invention is described as a "spinal" implant, the device can be adapted for use in other surgical procedures. The spinal implant, as described herein, provides a surgeon with a device that can easily and safely be inserted into the space previously occupied by the spinal disc. The spinal implant contains one or more magnets positioned on and/or within the device to self-align with one or more additional spinal implants inserted therein for the purpose of preventing misalignment of a plurality of implant devices during surgical procedures. Additionally, the magnets prevent or minimize the possibility of implant expulsion or migration, particularly for multiple implants that are inserted between vertebrae endplates having non-uniform or uneven surfaces.

Accordingly, it is an objective of the present invention to provide an improved spinal implant device which is useful in bone fusion/fixation surgeries.

It is a further objective of the present invention to provide an improved spinal implant device used for Posterior Lumbar Fusion (PLIF) procedures.

It is yet another objective of the present invention to provide an improved spinal implant device used for Transforaminal Lumbar Fusion (TLIF) procedures.

It is yet another objective of the present invention to provide an improved spinal implant device used for Anterior Lumbar Fusion (ALIF) procedures.

It is yet another objective of the present invention to provide an improved spinal implant device used for Extreme Lateral Interbody Fusion (XLIF) or Direct Lateral Interbody Fusion (DLIF).

It is a still further objective of the present invention to provide a self aligning spinal implant device which is useful in bone fusion/fixation surgeries.

It is a further objective of the present invention to provide a self centering spinal implant device which is useful in bone fusion/fixation surgeries.

It is yet another objective of the present invention to provide an improved spinal implant device comprising one or more magnets arranged to provide self-alignment with like configured spinal implant devices.

It is a further objective of the present invention to provide an improved spinal implant device comprising one or more magnets arranged to prevent or reduce implant expulsion or migration.

It is a further objective of the present invention to provide an improved spinal implant device which can be laterally stacked to form a predetermined geometrical shape.

It is a further objective of the present invention to provide an improved spinal implant device which can be laterally stacked to form anatomically dependent variable geometrical shapes.

It is yet another objective of the present invention to provide an improved spinal implant device which can be vertically stacked to form variable sized stackable units.

It is a further objective of the present invention to provide an improved spinal implant device which results in reduced inventory and shipping costs.

It is a further objective of the present invention to provide a kit having a plurality of self aligning spinal implant devices which can be vertically stacked to form a single unit having a predetermined height.

Other objectives band advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Referring to FIGS. 1-6, an illustrative embodiment of the spinal implant, preferably an interbody spinal implant device, in accordance with the present invention is shown. The spinal implant 10 is preferably suited for placement between adjacent human vertebral bodies. The implant 10 may be used in various spinal procedures, including but not limited to Anterior Lumbar Fusion (ALIF), Posterior Lumbar Fusion (PLIF), or Transforaminal Lumbar Fusion (TLIF), or Extreme Lateral Interbody Fusion (XLIF) or Direct Lateral Interbody Fusion (DLIF). The spinal implant 10 contains a body 12 having a top surface 14, a bottom surface 16, opposing lateral sides 18 and 20, and opposing anterior 22 and posterior 24 portions. Each of the top surface 14 and the bottom surface 16 may contain ridges or teeth (not shown) to aid in implant stability. The device 10 is preferably made of a durable material, such as stainless steel, stainless steel alloy, titanium, aluminum, an alloy, carbon fiber composite, or other durable materials such as but not limited to polymeric, ceramic, and composite materials. For example, certain embodiments of the present invention may be comprised of a biocompatible, polymeric matrix reinforced with bioactive fillers, fibers, or both. Certain embodiments of the present invention may be comprised of a high-performance engineering thermoplastic such as polyetherether-ketone (PEEK) or other polymers such as polyvinyl chloride (PVC), polyethylene, polyesters of various sorts, polycarbonate, Teflon coated metal or ultra high molecular weight polyethylene (UHMWPE). Certain embodiments of the present invention may be comprised of urethane dimethacrylate (DUDMA)/tri-ethylene glycol dimethacrylate (TEDGMA) blended resin and a plurality of fillers and fibers including bioactive fillers and E-glass fibers. Durable materials may also consist of any number of pure metals, metal alloys, or both. Titanium and its alloys are generally used due to their strength and biocompatibility.

Figure 1:
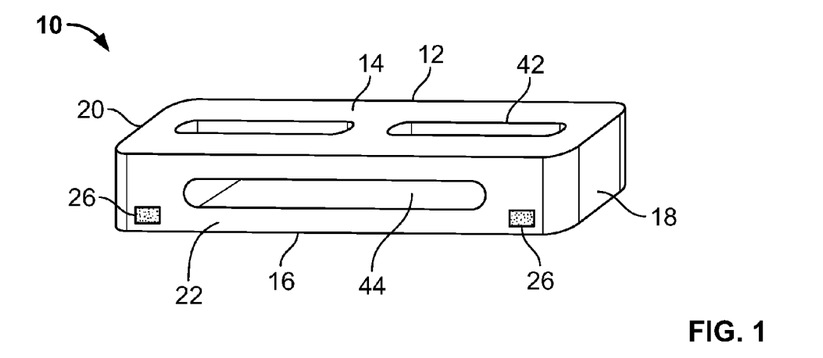
FIG. 1 is a front side perspective view of an illustrative embodiment of the spinal implant in accordance with the present invention.
Figure 2:
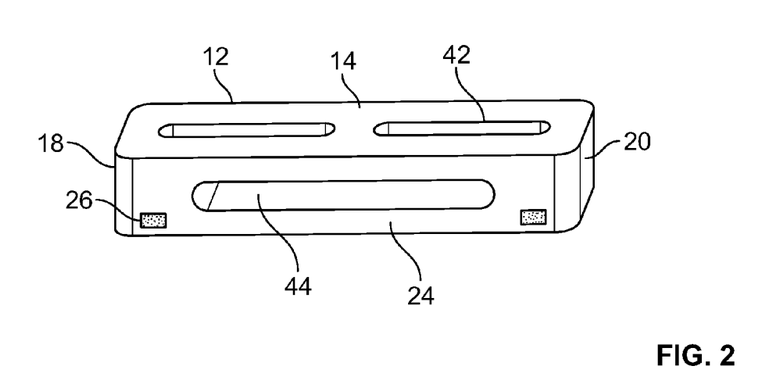
FIG. 2 is a back side perspective view of the illustrative embodiment of the spinal implant illustrated in FIG. 1.
Figure 3:
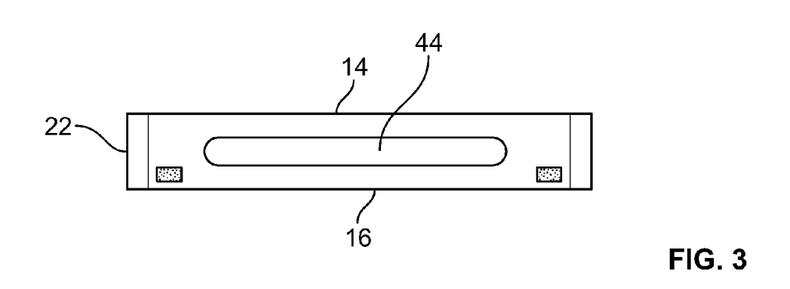
FIG. 3 is a side view of the illustrative embodiment of the spinal implant illustrated in FIG. 1.
Figure 4:
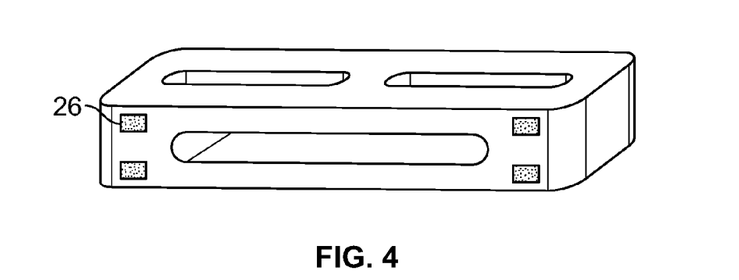
FIG. 4 is a perspective view of an alternative embodiment of the spinal implant in accordance with the present invention.
Figure 5:
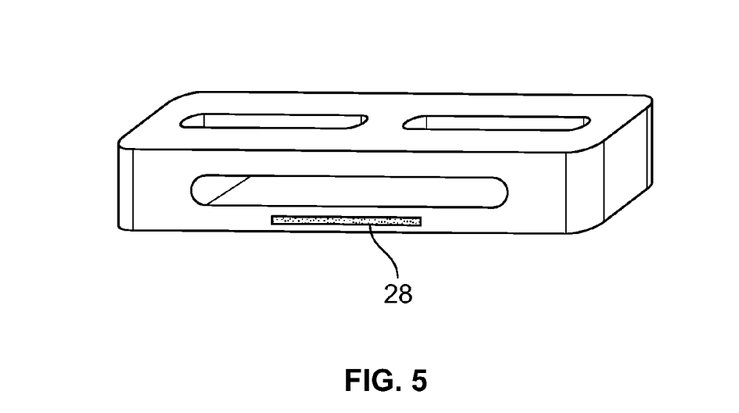
FIG. 5 is a perspective view of an alternative embodiment of the spinal implant in accordance with the present invention.

The body 12 of the spinal implant 10 contains one or more magnets 26 imbedded into the implant. The magnets 26 may be arranged to be an integral part of the outer surface of the top surface 14, the bottom surface 16, the opposing lateral sides 18 and 20, and the opposing anterior 22 and posterior 24 portions, or combinations thereof. As illustrated in FIGS. 1 and 2, magnets 26 are located at opposing ends of the anterior (FIG. 1) and posterior portion 24 (FIG. 2). FIG. 4 illustrates an alternative embodiment of the spinal implant 10 which contains a pair of magnets 26 located at one end of the anterior portion 22 and a pair of magnets along the opposing ends of the anterior portion 22. Referring to FIG. 5, individual magnets 26 are replaced by a magnetic bar 28.

Magnets 26 or magnetic bars 28 may be permanent magnets, temporary magnets, or electromagnets, and can be made from any material that produces a magnetic field and is insertable into a human which does not result in a biological or an immune reaction or that does not pose safety risks to the individual. As an illustrative example, the magnets may be rare-earth magnets made from alloys of rare earth materials, such as neodymium magnets. Such magnets may be encased by materials such as polyetherether-ketone (PEEK), parylene coatings, or ceramic coatings. Other forms of the magnet may be used; for example, a magnetic powder or nano-magnetic particles can be applied to one or more portions of the main body 14 or be incorporated within the material that comprises the body 12.

Figure 6:
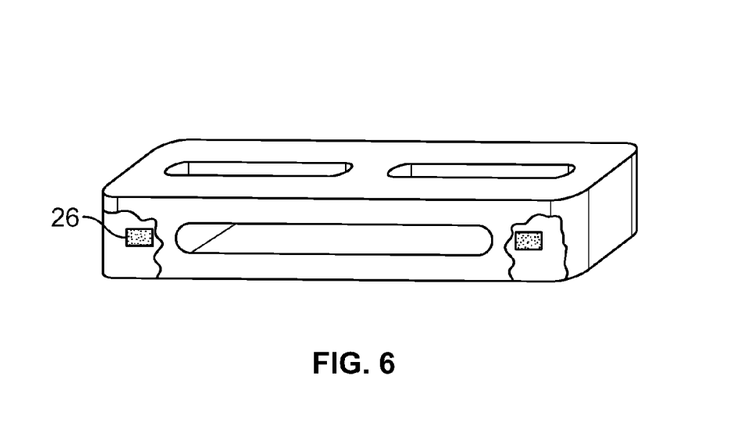
FIG. 6 is a perspective view of an alternative embodiment of the spinal implant in accordance with the present invention.

FIG. 6 illustrates an alternative embodiment of the spinal implant 10. In this embodiment, the magnet 26 or magnetic bar 28 (not illustrated) is integrally formed with the material that makes up the body 12. While the embodiments shown in FIGS. 1-6 illustrate the placement of the magnetic materials, either the magnets 26 or the magnetic bar 28, shown being placed along the anterior portion 22 or the posterior portion 24, or within the main body 12, such magnetic material can be placed anywhere along or within the top surface 14, the bottom surface 16, the opposing lateral sides 18 and 20, or combinations thereof.

Figure 10:
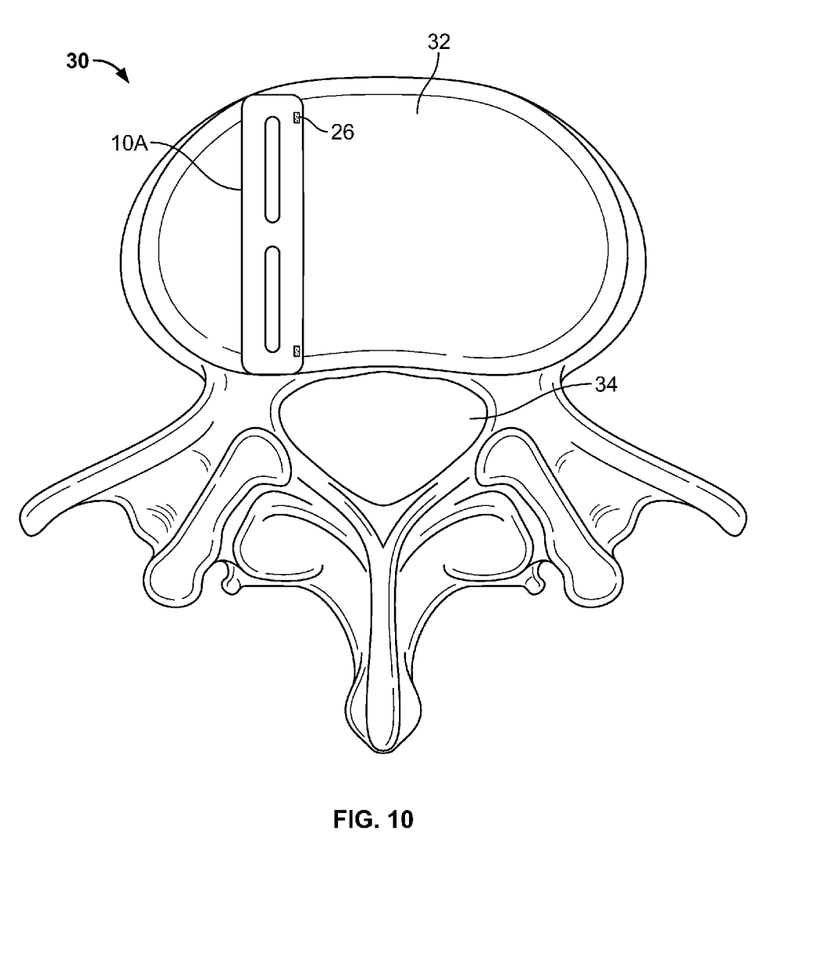
FIG. 10 illustrates implantation of a first spinal implant in accordance with the present invention within the disc space of adjacent vertebrae, resting on endplate.

Regardless of the positioning within or on the body 12, the magnets 26 or magnetic bar 28 provide a self-aligning function when two or more spinal implants 10 are aligned or placed at a proper distance so that the two or more spinal implants 10 are magnetically affected or drawn towards each other. Referring to FIG. 10, a top view of a vertebra 30 with an inserted first spinal implant 10A is illustrated. As shown, the vertebral disc has been removed to expose the vertebral endplate 32. The spinal chord, not illustrated, runs through the spinal canal 34. A single spinal implant 10 is shown inserted in between opposing endplates, not shown, and resting on endplate 32. Use of implants having magnets overcomes some of the problems associated with implanting multiple implants. For example, when an individual undergoes removal of the disc, it is a common procedure for the surgeon to prepare the endplate for insertion therein. Part of the preparation includes scraping of the endplate to provide a smooth surface for the implant to rest upon. However, the surface of the endplate is not always uniform, even with surgical preparation intervention. This presents a problem or insertion of multiple implants where the first implant is tightly secured between adjacent endplates but a remote portion of the endplate or an adjacent second endplate does not provide such a tight fit for the second implant because of the non-uniform nature of the endplate surface. The second implant is subject to floating, in which the second implant may move from its original implant site, risking sliding into the spinal canal or nerve roots, subjecting the patient to increased risk of serious damage.

Figure 11:
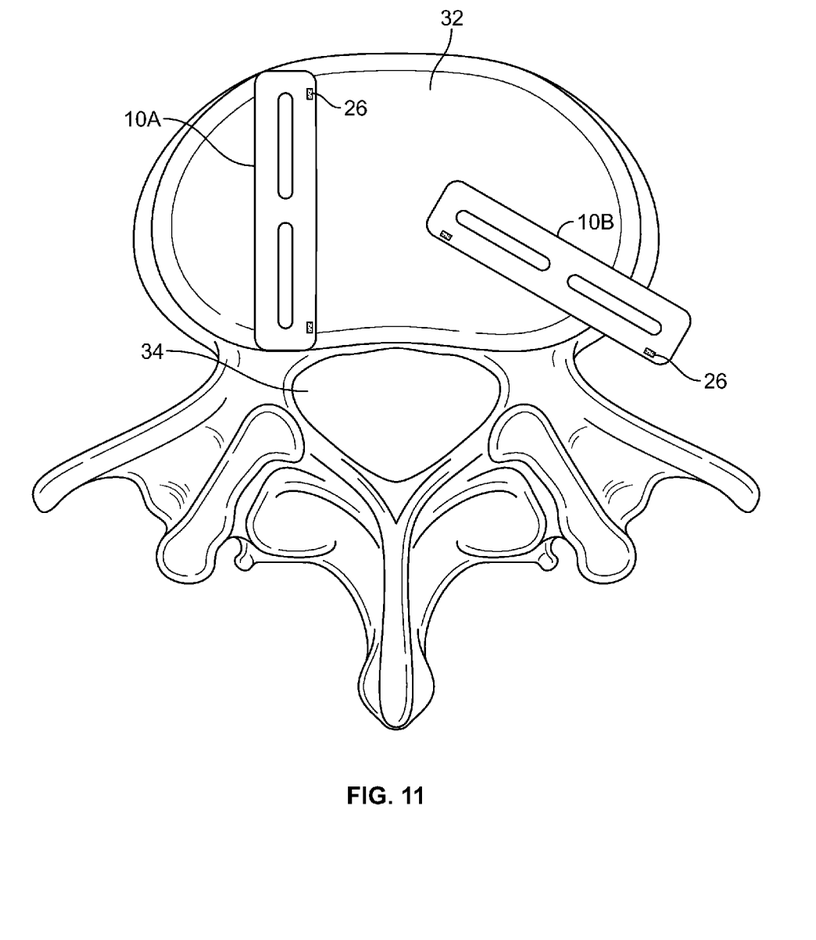
FIG. 11 illustrates implantation of a second spinal implant in accordance with the present invention within the disc space of adjacent vertebrae.
Figure 12:
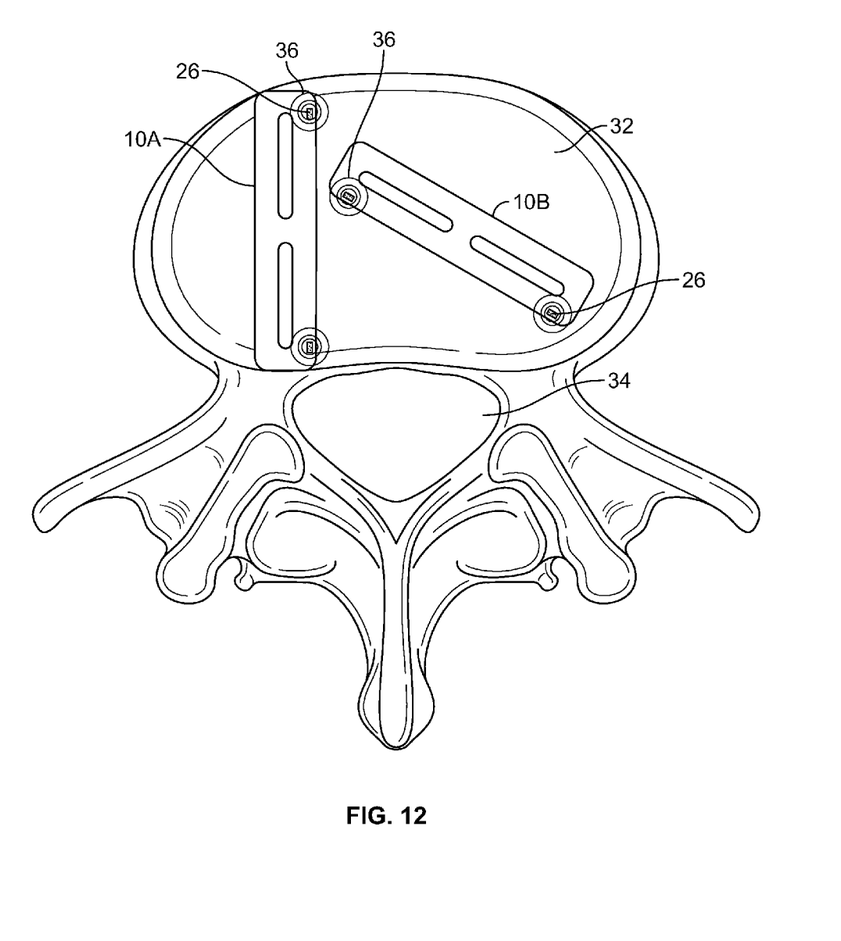
FIG. 12 illustrates the second spinal implant in accordance with the present invention further being moved into close proximity with the first spinal implant.

In bone fusion surgeries not using the spinal implant 10 in accordance with the present invention, inserting a second implant and aligning with a first spinal implant requires manipulation; there is no guarantee that correct alignment can be accomplished. However, using an implant in accordance with the present invention, self-alignment and self-centering can be accomplished. Referring to FIG. 11, as the second spinal implant 10B is inserted in between adjacent vertebrae, the surgeon is required to manipulate the spinal implant 10B until it is in close proximity to be affected by the magnetic fields 36 of the magnets 26 of spinal implant 10A, see FIG. 12. Once in close proximity, the magnetic field 36 of the second spinal implant 10B is drawn to the magnetic field 36 of the first spinal implant 10A.

Figure 13:
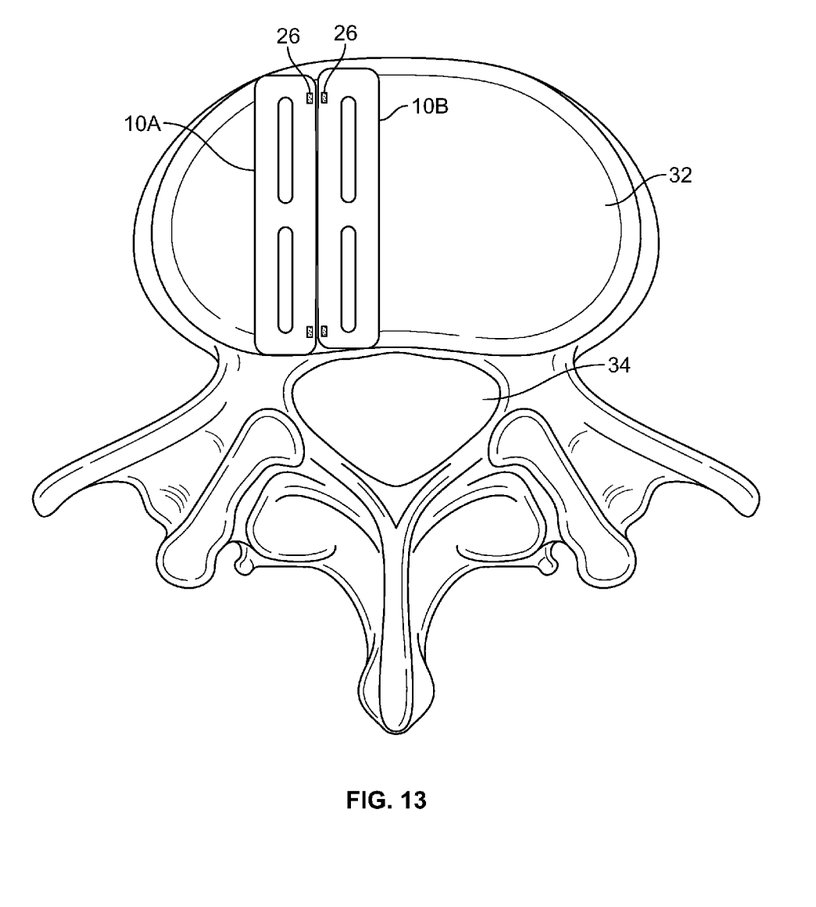
FIG. 13 illustrates the first and second spinal implant in a self-aligning arrangement.
Figure 14:
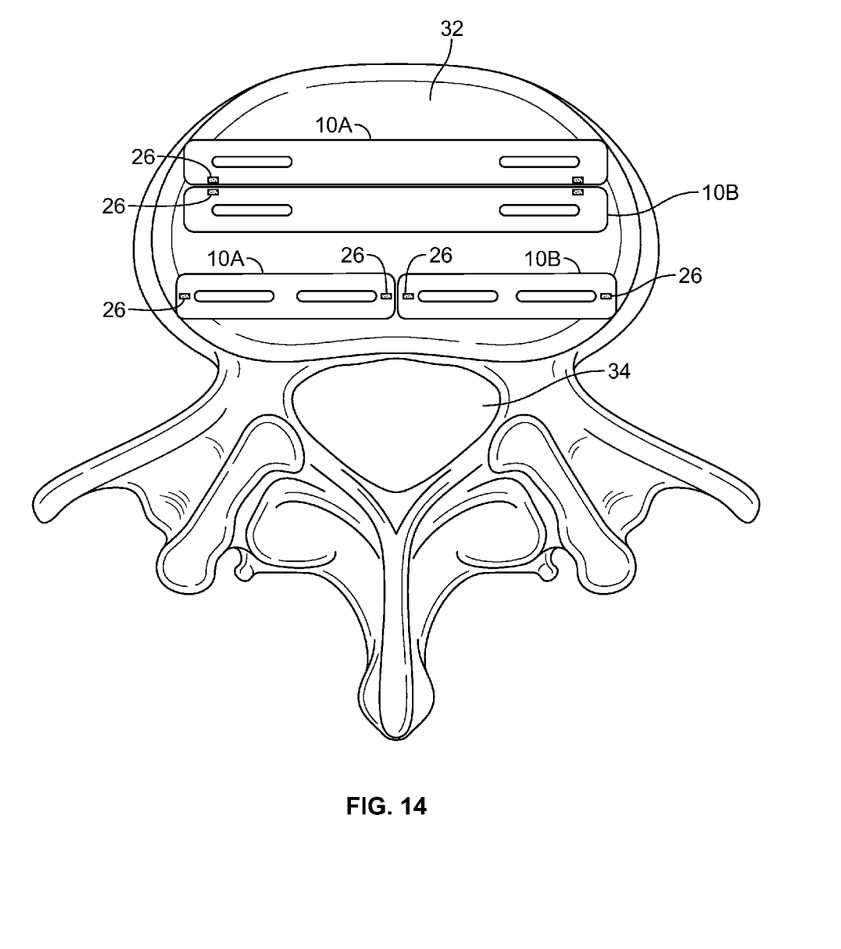
FIG. 14 illustrates the first and second spinal implant arranged in a different orientation within the disc space of adjacent vertebrae.

Accordingly, the magnets 26 cause the second spinal implant 10B to self align and self center with the first spinal implant 10A, see FIG. 13. In order to achieve the self-aligning and self-centering function, it is critical that the polarity of the magnets 26 on the spinal implant 10A are arranged so as to respond to the magnetic field produced by the magnets 26 of the spinal implant 10B. The two spinal implants 10A and 10B are aligned along their anterior 22 and posterior 24 sides, but could be arranged so that opposing sides 18 and 20, or the top surface 14 and bottom surfaces 16 align. This capability allows the spinal implants 10A and 10B to be arranged in different orientations, such as vertical alignment across the endplates arranged side to side or end to end, see FIG. 14, as opposed to horizontally aligned across the endplates. In any orientation, the spinal implants 10A and 10B self-align. While not illustrated, additional spinal implants may be inserted.

Figure 7:
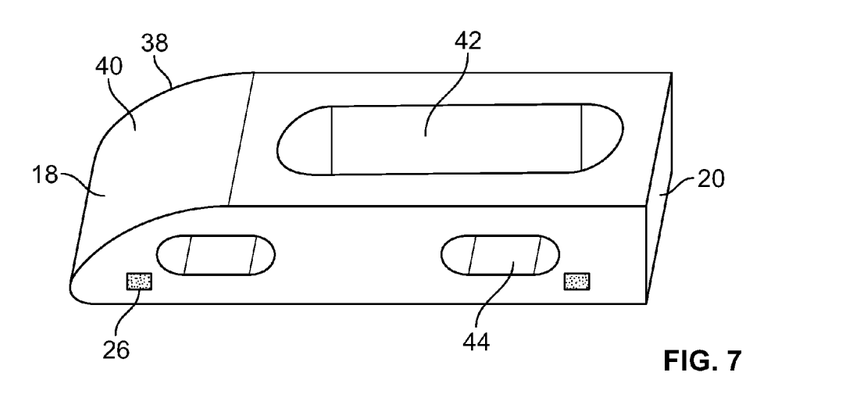
FIG. 7 is a perspective view of an alternative embodiment of the spinal implant in accordance with the present invention.
Figure 8:
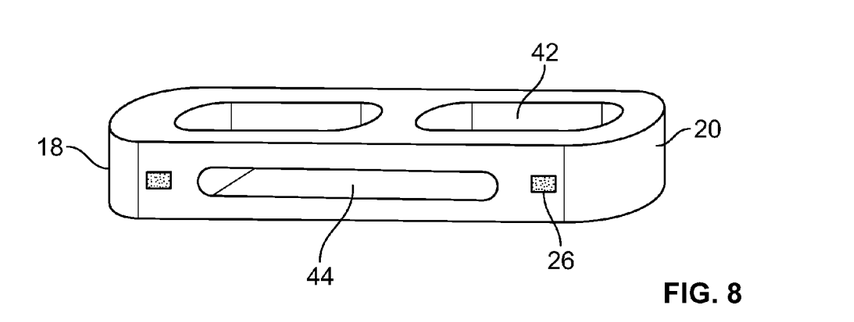
FIG. 8 is a perspective view of an alternative embodiment of the spinal implant in accordance with the present invention.
Figure 9:
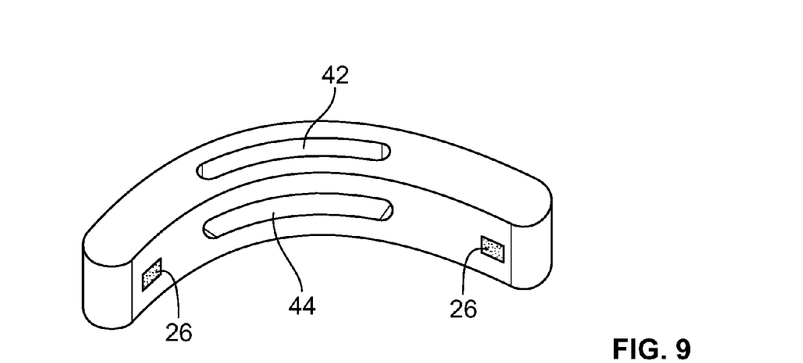
FIG. 9 is a perspective view of an alternative embodiment of the spinal implant in accordance with the present invention.

Referring back to FIGS. 7-9, alternative embodiments of the spinal implants 10 are shown. The size and shape of the spinal implant 10 can be varied depending on the type of surgical procedure undertake, the size and shape of the individual's vertebrae, the type of procedure used (for example PLIF or TLIF), or vertebral separation and/or support. The spinal implant 10 may also contain additional features that aid in implantation. For example, FIG. 7 illustrates a spinal implant 10 in which one of the opposing ends 18 contains a curved surface 38, forming an angled or ramped surface area 40. FIG. 8 illustrates a spinal implant 10 in which opposing sides 18 and 20 are curved. Referring to FIG. 9, the main body 12 is shown having a half-moon or crescent shape. Each of the embodiments shown in FIGS. 7-9, as well as those illustrated in FIGS. 1-6 may contain cancellous autograft bone, allograft bone, demineralized bone matrix (DBM), porous synthetic bone graft substitutes, bone morphogenic proteins (BMP), or combinations thereof, inserted within a hollow portion of the spinal implant 10. Additionally, the spinal implant 10 may contain one or more vertical apertures 42 and one or more traverse apertures 44 sized and shaped to maximize access to bone graft material provided within the implant 10. An additional opening (not illustrated) may be utilized to facilitate manipulation of the implant 10 by a surgical tool.

Figure 15A:
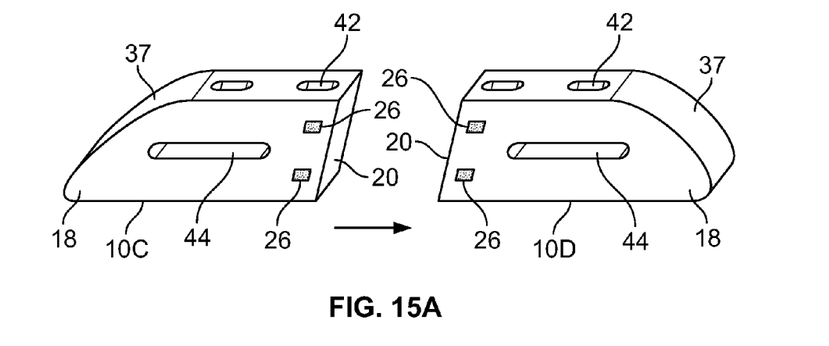
FIG. 15A illustrates a plurality of spinal implants prior to being laterally stacked to form a geometrical shape in the form of a trapezoid.
Figure 15B:
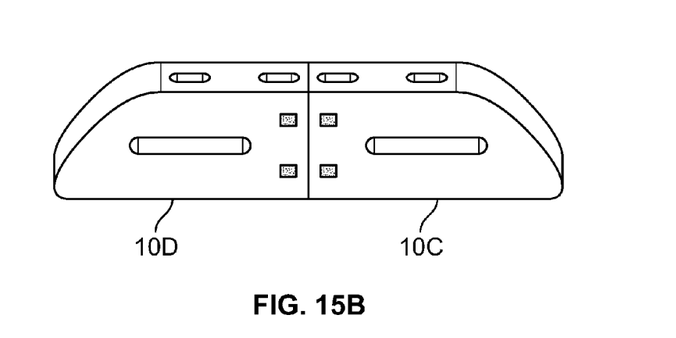
FIG. 15B illustrates the plurality of spinal implants illustrated in FIG. 15A laterally stacked to form a geometrical shape in the form of a trapezoid.
Figure 15C:
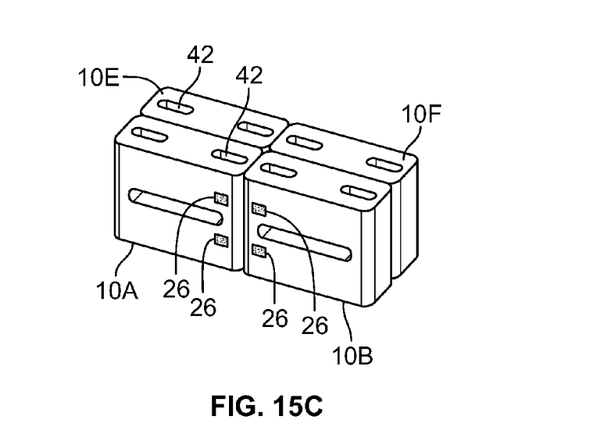
FIG. 15C illustrates a plurality of spinal implants laterally stacked to form a geometrical shape in the form of a square.

One of the unique features of the spinal implant 10 in accordance with the present invention is that a plurality of implants can be arranged to provide a predetermined shape, height, or combinations thereof, prior to or at the time of performing a surgical procedure. As such, the spinal implant 10 can be either laterally or vertically stacked to achieve such purposes. Referring to FIGS. 15A-15C, spinal implants are shown arranged and secured to each other to form a predetermined shape. By laterally stacking each of the spinal implants, the user can form variable geometrical shapes which are dependent on the anatomical structure of the patient. Such variable geometrically shaped formation provides an advantage in situations where the anatomical structures are not ideal or are diseased causing irregularly shaped features. Moreover, because the spinal implants 10 are self-aligning or can be secured to adjacent spinal implants based on magnetic principles, the geometrical shapes can be formed at the time of the surgical implant procedure and inserted into the graft site. The ability to form a desired shape provides the surgeon the ability to customize the implant shape to fit the contours of the vertebrae. Alternatively, the spinal implants 10 can be pre-assembled to a pre-determined shape prior to a surgical procedure.

Given the ability to secure to adjacent implants, any number of geometrical shapes can be formed. For example, FIGS. 15A and 15B illustrate spinal implants 10C and 10D having an end 18 which has tapering or inclined surface 37. Securing each implant so that the tapered ends 37 face outwardly provides a generally trapezoidal shape, see FIGS. 15A and 15B. Alternative shapes, such as the square shaped configuration of spinal implants 10A, 10B, 10E and 10F shown in FIG. 15C, may be formed. Such functioning allows for a modular spinal implant system that can be pre-packaged and shipped to a user. Such pre-packaging could include individual spinal implant units that have been sterilized, thereby allowing the user the ability to assemble each implant to a desired height, configuration, or combinations thereof on field. As described previously, the shapes can be formed in vitro during the surgical procedure, or can be assembled ex vivo, and shipped in a pre-packaged configuration having a desire shape and inserted into the anatomical landscape.

Figure 16A:
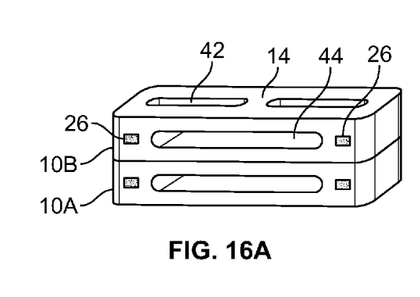
FIG. 16A illustrates vertical stacking of two spinal implants.
Figure 16B:
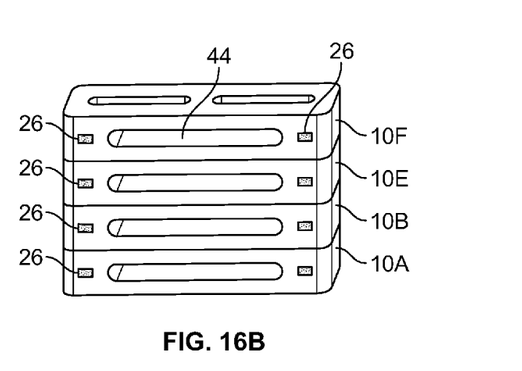
FIG. 16B illustrates vertical stacking of a plurality of spinal implants.
Figure 16C:
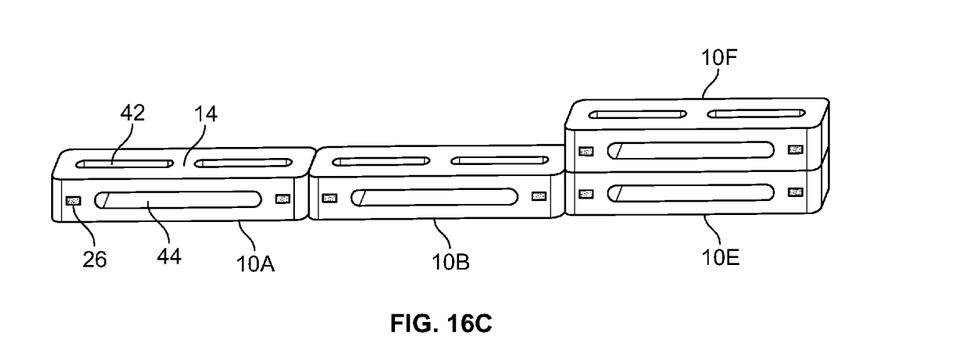
FIG. 16C illustrates a combination vertical and lateral stacking of the spinal implants.
Figure 16D:
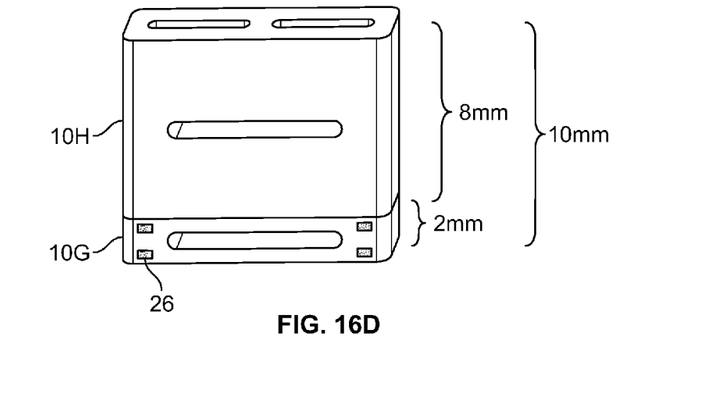
FIG. 16D illustrates two spinal implants of variable sized stacked together.

In addition to lateral stacking, the spinal implants 10 can be vertically stacked, see FIG. 16A or 16B. As seen in FIG. 16A, two spinal implants 10A and 10B are illustrated in a vertically stacked position in which spinal implant 10B rests on top of spinal implant 10A. FIG. 16B illustrates a plurality of spinal implants, 10A, 10B, 10E, and 10F in a vertically stacked arrangement. In this configuration, each adjacent spinal implant not only secures to the spinal implant above and below, but also is maintained in a correct spatial alignment so that none of the spinal implants overhang or are misaligned with the other spinal implants. This arrangement ensures that the stacked spinal implants form a flush, single unit comprising of multiple, independent implants. By providing for such functionality, the user can stack one or more sized implant to achieve a larger size. For example, standard sized implant devices can range from 2 mm, 4 mm, 6 mm, 8 mm, 10 mm, or 20 mm in size. Typically, spinal implant companies provide surgeons with a plurality of differently sized implants for each procedure. Having to package and ship a large number of spinal implants, each having different sizes, is costly. Moreover, the surgeon may not actually utilize all of the implant sizes. However, such costs can be avoided as the spinal implants in accordance with the present invention can be vertically stacked to form a secondary, larger sized implant. For example, instead of packaging and shipping a 10 mm, 12 mm, or 20 mm sized spinal implant, a 6 mm and a 4 mm sized implant can be vertically stacked to form a size 10 spinal implant. FIG. 16D illustrates two spinal implants 10G and 10H which when stacked together form a "larger" implant. As illustrated, spinal implant 10G is a 2 mm implant; spinal implant 10H is an 8 mm implant. When stacked together, the combination of the two form a 10 mm structure.

In a typical surgical setting, the surgeon is usually forced to obtain numerous spinal implants varying in size. Having a plurality of smaller sized implants which can be vertically stacked together not only reduces the inventory and shipping costs, but the surgeon will also be capable of creating a specific spinal implant height onsite during the surgical procedure. Additionally, the surgeon can utilize a combination of laterally stacked spinal implants, 10A and 10B with a plurality of vertically stacked implants 10E and 10F, see FIG. 16C. This arrangement allows the surgeon the ability to build up certain areas of an implant site relative to other areas. This may be important for implant sites that contain depressions or erosion within the bone.

Figures 17A, 17B:
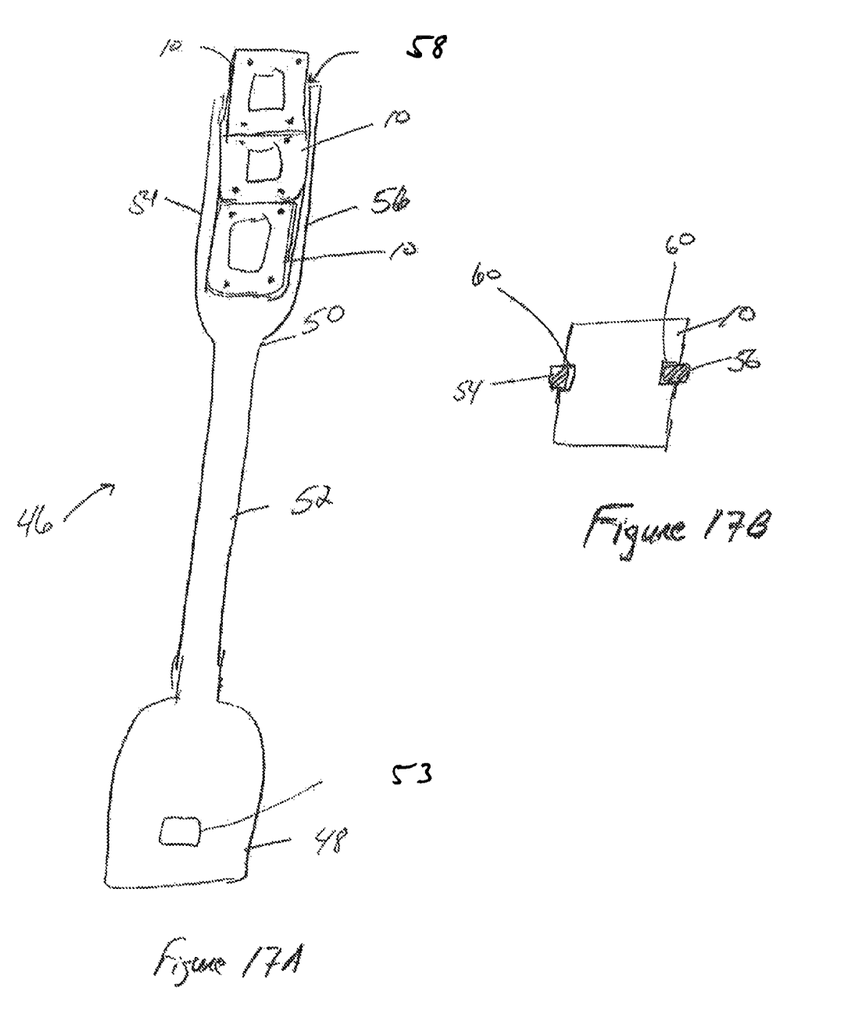
FIG. 17A is a perspective view of an illustrative embodiment of a spinal implant holder and insertion device having a plurality of spinal implants.
FIG. 17B is a top view of the spinal implant holder and insertion device having a plurality of spinal implants illustrated in FIG. 17A.

Referring to FIG. 17A, an illustrative example of spinal implant holder and insertion device 46 a spinal implant holder and insertion device 46 is constructed and arranged to provide a tool to assist the surgeon during insertion of the insert the spinal implant 10, whether inserted as an individual units or as a pre-assembled structure. The spinal implant holder and insertion device 46 may contain a proximal end 48, a distal end 50, and a main body 52 therebetween. The distal end 50 contains a pair of prongs 54 and 56. The prongs 54 and 56 are arranged in a generally parallel manner and spaced apart to form a spinal implant holding area 58. The spinal implant holding area 58 is sized and shaped to receive and hold at least one spinal implant 10. Preferably, the spinal implant holder and insertion device 46 is designed to allow for at least one of the prongs 54 or 56, to separate from the other to allow for insertion or removal from the spinal implant holding area 58. Alternatively, both prong 54 and 56 can be adapted to move and separate from each other. The proximal end 48 may contain an actuating button 53 adapted to provide separation and/or closure of prongs 54 and 56. Spinal implants 10 may contain grooves or channels 60 sized and shaped to receive at least a portion of prongs 54 and 56, thereby securing the spinal implant within the spinal implant holding area 58.

Figure 18:
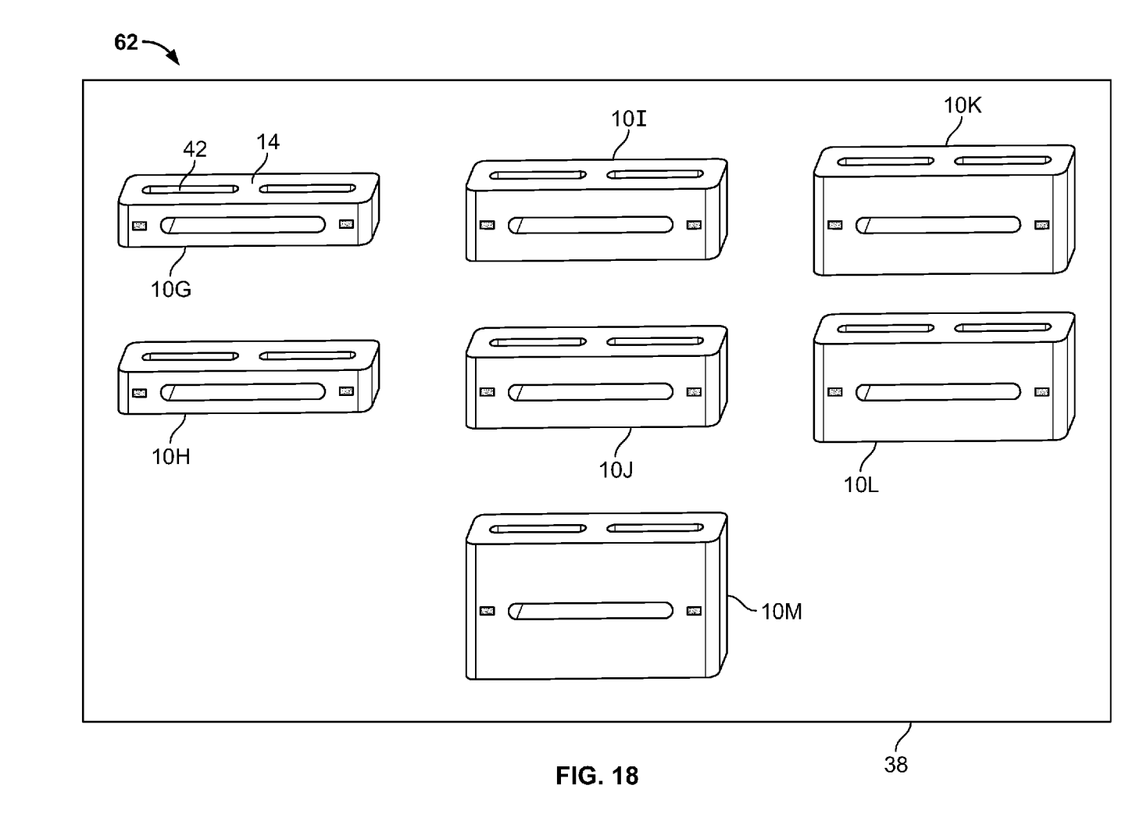
FIG. 18 is an illustrative example of a kit including a plurality of spinal implants having variable sizes.

FIG. 18 illustrates a plurality of spinal implants arranged in a kit 62. The kit 62 includes a housing structure constructed and arranged to hold a plurality of variable sized spinal implants 10G-10M. As an illustrative example, the kit 36 may contain two size 2 mm spinal implants 10G, 10H, two size 4 mm spinal implants 101, 10J, two size 6 mm spinal implants 10K, 10L, and one size 8 mm spinal implant 10M. Using this kit, the surgeon has a plurality of spinal implants from which to form vertically stack units, easily building the spinal implants to 10G-10M a desired height. While a kit may be employed, each individual spinal implant 10 may be pre-sterilized and pre-packaged individually.

Although the present invention has been described in the spinal surgical setting, the implant devices can be adapted to be used in other surgical settings, such as orthopedic implants for orthopedic surgeries.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A system of spinal implants, comprising:
    a self-aligning insertion body comprised of a plurality of implant bodies each having a top surface, bottom surface, first lateral side portion, second lateral side portion, anterior side portion, and posterior side portion;
    a first of the plurality of implant bodies having a first magnet embedded in the anterior side portion adjacent each of the first lateral side and top surface, a second magnet embedded in the anterior side portion adjacent each of the first lateral side portion and bottom surface, a third magnet embedded in the anterior side portion adjacent each of the second lateral side portion and top surface, and a fourth magnet embedded in the anterior side portion adjacent each of the second side portion and bottom surface;
    a second of the plurality of implant bodies having a fifth magnet embedded in the posterior side portion adjacent each of the first lateral side and top surface, a sixth magnet embedded in the anterior side portion adjacent each of the first lateral side portion and the bottom surface, a seventh magnet embedded in the posterior side portion adjacent each of the second lateral side portion and the top surface, and an eighth magnet embedded in the posterior side portion adjacent each of the second lateral side portion and the bottom surface;
    wherein the plurality of implant bodies are stacked to form the self-aligning insertion body prior to or at the time of performing a surgical procedure; and
    wherein each implant body further comprises at least one aperture on the top surface, such that a hollow cavity is defined within the implant body.

2. The system of claim 1, wherein the plurality of implant bodies are laterally stacked to form an anatomically dependently shaped self-aligning insertion body.

3. The system of claim 1, wherein the plurality of implant bodies are vertically stacked to form an anatomically dependently shaped self-aligning insertion body.

4. The system of claim 1, wherein the plurality of implant bodies are secured and maintained in correct spatial alignment via attractive forces created by the magnets.

5. The system of claim 1, wherein each of the first, second, third, fourth, fifth, sixth, seventh, and eighth magnets are rare-earth magnets.

6. The system of claim 5, wherein the rare earth magnets are neodymium magnets.

7. The system of claim 1, wherein the plurality of implant bodies are made from a polymer.

8. The system of claim 7, wherein the polymer is polyetherether-ketone.

* * * * *